United States Patent
Li et al.

(10) Patent No.: US 9,970,917 B2
(45) Date of Patent: *May 15, 2018

(54) USE OF SILK NUMBER ASSAY TO SCREEN FOR GENES ENHANCING CORN YIELD

(71) Applicant: PIONEER HI BRED INTERNATIONAL, INC., Johnston, IA (US)

(72) Inventors: Guofu Li, Johnston, IA (US); Junli Ji, Des Moines, IA (US)

(73) Assignee: PIONEER HI-BRED INTERNATIONAL, INC. IA (US)

(*) Notice: Subject to any disclaimer, the term of this patent is extended or adjusted under 35 U.S.C. 154(b) by 69 days.

This patent is subject to a terminal disclaimer.

(21) Appl. No.: 14/873,271

(22) Filed: Oct. 2, 2015

(65) Prior Publication Data

US 2016/0041140 A1  Feb. 11, 2016

Related U.S. Application Data

(63) Continuation of application No. 13/602,548, filed on Sep. 4, 2012, now Pat. No. 9,206,437, which is a continuation-in-part of application No. 12/647,572, filed on Dec. 28, 2009, now abandoned.

(60) Provisional application No. 61/141,115, filed on Dec. 29, 2008.

(51) Int. Cl.
*A01H 1/04* (2006.01)
*G01N 33/00* (2006.01)
*C12N 15/82* (2006.01)

(52) U.S. Cl.
CPC ........... *G01N 33/0098* (2013.01); *A01H 1/04* (2013.01); *C12N 15/8261* (2013.01)

(58) Field of Classification Search
None
See application file for complete search history.

(56) References Cited

U.S. PATENT DOCUMENTS 9,206,437 B2 * 12/2015 Li .......................... A01H 1/04
2007/0169225 A1 * 7/2007 Bruce .................. C07K 14/415
800/287

* cited by examiner

Primary Examiner — Stuart F Baum

(57) ABSTRACT

The invention provides a rapid and efficient method and assay for monitoring yield enhancement in a plant using a measure of silk number. The plant is transformed with a prospective gene associated with yield enhancement. The transformed plant is grown along with non-transformed control plants until silk growth is apparent. The change in the number of silks in the transformed plant correlated to the change in yield for the plant. Therefore, changes in yield enhancement can be estimated in the transformed plant prior to harvest of mature plant tissues.

5 Claims, 2 Drawing Sheets

USE OF SILK NUMBER ASSAY TO SCREEN FOR GENES ENHANCING CORN YIELD

CROSS REFERENCE

This utility application is a continuation application of U.S. Ser. No. 13/602,548, filed Sep. 4, 2012, now U.S. Pat. No. 9,206,437, which is a continuation-in-part of U.S. patent application Ser. No. 12/647,572, filed Dec. 28, 2009, now abandoned and claims the benefit U.S. Provisional Application Ser. No. 61/144,115, filed Dec. 29, 2008, each of which are incorporated herein by reference.

TECHNICAL FIELD

The present invention relates generally to plant molecular biology. More specifically, it relates to methods for measuring yield/yield potential in plants.

BACKGROUND OF THE INVENTION

Seed yield is a very complex trait and can be further dissected into several component traits, which are controlled by many interacting factors and pathways. Genes contributing to a complex crop trait such as yield can be numerous, making it extremely difficult to find genes that could be used to enhance yield through low throughput transgene discovery and validation process.

Additionally, grain yield in *Zea mays* is dependent upon the number of ovaries which are initiated, are fertilized and develop to maturity. Reduced grain production may result from, inter alia, a decrease in the number of kernel initials, restricted or untimely silk exsertion and/or kernel abortion during grain development. Maize silks comprise the stigmatic tissues of the flower, intercepting air-borne pollen and supporting pollen tube growth to result in fertilization. Importantly, the process of fertilization determines kernel number and thus sets an irreversible upper limit on grain yield.

One of the important keys to successful high throughput (HTP) evaluation of yield enhancing genes is the ability to eliminate genes that do not positively affect yield. However, measuring yield has been proven difficult because of the huge variation in yield associated with pollination and magnified plant to plant variation in greenhouse studies. This invention describes a new approach that is able to circumvent these problems and that makes the HTP evaluation of yield enhancing genes feasible.

SUMMARY OF THE INVENTION

Generally, it is an object of the present invention to provide methods for measuring yield enhancing gene expression in a growing plant. The surrogate T1 yield assay detailed in this invention is sensitive enough to differentiate 10% difference in silk number between T1 transgenic and null plants at P<0.1 in the greenhouse environment and can be used to identify yield enhancement lead through Pioneer's high throughput transgene evaluation system, which make it easier to screen thousands of genes to find a few that by themselves or in combination could significantly increase yield in various environmental conditions.

DETAILED DESCRIPTION OF THE INVENTION

The present invention relates to a HTP screening and validation method for identifying constructs that may be used to enhance yield or yield potential. The method combines the high throughput transgene function analysis (US Patent Application Publication Number 2007/0186313 A1) with the high throughput T1 phenotyping described in this invention in a defined growth condition. The method uses a high throughput silk number determination assay at a defined developmental stage of the test plants to evaluate the yield potential in a defined growing condition.

The method determines the effect of transgene of yield or yield potential early in the transgene evaluation process. It allows us to predict the enhancement of a transgene on harvestable yield in T1 generation, without going through the time consuming yield trial process.

T1 Plants to be Evaluated

The constructs evaluated in T1 silk number assay are selected based on their performance in yield related traits at T0 generation. T1 seeds are generated by crossing T0 hemizygous plants by fast growing, short stature inbred.

Growing Conditions

Each T1 plant is grown in a classic 200 size pot (volume equivalent to 1.7 L) labeled with a bar coded label with information about the plant's genetic identity, planting date and greenhouse location. The planting density is 8.5" between plants (~72K plants/acre). T1 seeds are sown in 50% Turface and 50% SB300 soil mixture at a uniform depth of 2" from the surface. Transgenic plants and their non-transgenic segregants were identified through strip test, assaying the presence of a marker gene linked with gene of interest.

Experimental Design

A nested block design with stationary blocks was used to minimize spatial variation. Experiment is blocked by events and constructs. Multiple events were evaluated for each constructs. For each event 15 transgene positive plants and 11 to 12 transgene negative plants were used. Positives and negatives are completely randomized within each event block. The transgene negative plants from events of the same construct were pooled together and used as construct null.

Silk Cutting

Silk was harvested at 8 days after silking using a cutting device. The silk pieces are deposited in a 20 ml scintillation vial temporarily attached to the cutting device. Residual silk pieces are rinsed into the vial with ~10 ml 90% ethanol applied by hand from a squirt bottle. The alcohol rinse here not only ensures that all silks are deposited in the vial but also reduces build up of sugary residues on the blades. Vials are labeled by writing EU-ID on the vial or alternatively the vials can be pre-labeled with bar codes containing info needed for sampled recognition.

Silk Number Determination

Silk number determination was carried out using ImagePro silk counting software. For each sample, the contents of the vial are poured into a glass Petri dish 7.5 cm diameter and with walls 14 mm high, placed on dark navy blue or black background under a digital CDD (Q-imaging) camera connected to a PC equipped with ImagePro. The layer of liquid should be about 0.5 cm deep. Any contaminations such as anthers or husk tips are removed. The sample is allowed to settle for 5 seconds before the imaging.

Other Parameters Collected During T1 Yield Assay

In addition to silk numbers, scientists collected other data for parameters such as specific growth rate and maximum total area. The specific growth rate is the plant growth rate during exponential growth period. Maximum total area are the maximum biomass based on the three dimensional imaging of Lemna Tec. Shedding and silking data are also collected.

BRIEF DESCRIPTION OF THE FIGURES

FIG. 2a indicates 4 days, FIG. 2b illustrates 6 days and FIG. 2c shows 8 days after silking.

DEFINITIONS

Figure 1:
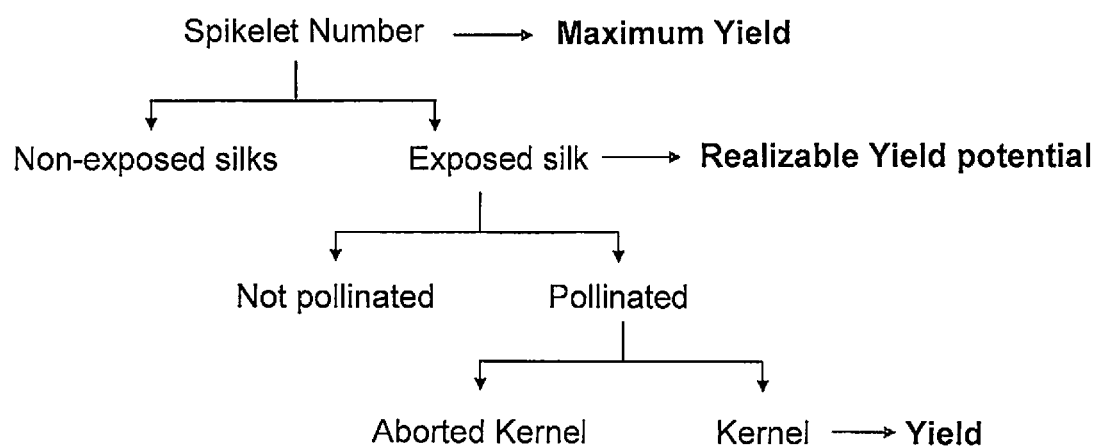
FIG. 1 shows a diagram illustrating the process from spikelet to kernel, showing the relationship between spikelet number, exposed silk number and kernel numbers.

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting. The following is presented by way of illustration and is not intended to limit the scope of the invention.

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges recited within the specification are inclusive of the numbers defining the range and include each integer within the defined range. Amino acids may be referred to herein by either their commonly known three-letter symbols or by the one-letter symbols recommended by the IUPAC-IUBMB Nomenclature Commission. Nucleotides, likewise, may be referred to by their commonly accepted single-letter codes. Unless otherwise provided for, software, electrical and electronics terms as used herein are as defined in The New IEEE Standard Dictionary of Electrical and Electronics Terms (5$^{th}$ edition, 1993). The terms defined below are more fully defined by reference to the specification as a whole. Section headings provided throughout the specification are not limitations to the various objects and embodiments of the present invention.

In accordance with the present invention, methods and assays are described for measuring enhanced yield by plants and for the identification of candidate polynucleotides that modulate yield. Without wishing to be bound by this theory, plants having polynucleotides that increase silk number are believed to have increased yield and/or biomass. Methods and assays of the present invention use a measurement of silk number as a correlated measure of yield enhancement.

The term "plant" includes but is not limited to a plant cell, a plant protoplast, plant cell tissue culture from which a plant can be regenerated, plant calli, a plant clump and a plant cell that is intact in plants or parts of plants such as an embryo, seed, root, root tip and the like.

A "subject plant" refers to a plant that is being screened for yield enhancement.

A "control plant" may comprise, for example: (a) a wild-type plant, i.e., of the same genotype as the starting material for the genetic alteration which resulted in the subject plant or cell; (b) a plant of the same genotype as the starting material but which has been transformed with a null construct (i.e., with a construct which has no known effect on the trait of interest, such as a construct comprising a marker gene) or (c) a plant which is a non-transformed segregant among progeny of a subject plant. Thus, a "control plant" provides a reference point for measuring changes in phenotype of the subject plant, for example, a difference in the number of silks formed in the control plant as compared to the number of silks formed the subject plant.

As used herein, "yield" may include reference to bushels per acre of a grain crop at harvest, as adjusted for grain moisture (15% typically for maize, for example), and the volume of biomass generated (for forage crops such as alfalfa, and plant root size for multiple crops). Grain moisture is measured in the grain at harvest. The adjusted test weight of grain is determined to be the weight in pounds per bushel, adjusted for grain moisture level at harvest. Biomass may be measured as the weight of harvestable plant material generated. One skilled in the art will be able to determine yield or biomass for a particular plant.

As used herein, "polynucleotide" includes reference to a deoxyribopolynucleotide, ribopolynucleotide or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Thus, DNAs or RNAs with backbones modified for stability or for other reasons are "polynucleotides" as that term is intended herein. Moreover, DNAs or RNAs comprising unusual bases, such as inosine or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

As used herein, the term "modulate", "modulates" or "modulating" refers to a change, i.e., an increase or decrease in the silk number correlating with plant yield.

Any plant may be screened using the methods and assays described herein, including but not limited to transgenics, inbreds, hybrids and non-transformed plants. This also includes plants that have been treated with a mutagen, such as ethyl methanesulfonate (EMS) and the like. In one aspect, the plant to be screened includes a candidate polynucleotide suspected of modifying yield of the plant. In another aspect, the plant comprises individual or combinations of genes to be screened for their effect on yield.

Using methods or assays of the present invention, one skilled in the art would be able to screen thousands of different plants, for example, for gene expression causing enhanced yield. The methods of the present invention are useful for a variety of applications. These plants may be additionally screened for their ability to increase the yield or biomass of a plant as compared to a control. The present invention provides for a high throughput assay for screening a plurality of plants to identify a plant with enhanced yield.

By "encoding" or "encoded", with respect to a specified nucleic acid, is meant comprising the information for translation into the specified protein. A nucleic acid encoding a protein may comprise intervening sequences (e.g., introns) within translated regions of the nucleic acid, or may lack such intervening sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum* or the ciliate *Macronucleus*, may be used when the nucleic acid is expressed therein.

When the nucleic acid is prepared or altered synthetically, advantage can be taken of known codon preferences of the intended host organism. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray, et al., (1989) *Nucl. Acids Res.* 17:477-498). Thus, the maize-preferred codon for a particular amino acid may be derived from known gene sequences from maize. Maize codon usage for 28 genes from maize plants is listed in Table 4 of Murray, et al., supra.

As used herein "full-length sequence" in reference to a specified polynucleotide or its encoded protein means having the entire amino acid sequence of a native (non-synthetic), endogenous, biologically (e.g., structurally or catalytically) active form of the specified protein. Methods to determine whether a sequence is full-length are well known in the art, including such exemplary techniques as northern or western blots, primer extension, S1 protection, and ribonuclease protection. See, e.g., *Plant Molecular Biology: A Laboratory Manual*, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNNAUGG, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by human intervention.

By "host cell" is meant a cell which contains a vector and supports the replication and/or expression of the vector. Host cells may be prokaryotic cells such as *E. coli*, or eukaryotic cells such as yeast, insect, amphibian or mammalian cells. Preferably, host cells are monocotyledonous or dicotyledonous plant cells. A particularly preferred monocotyledonous host cell is a maize host cell.

The term "introduced" includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA). The term includes such nucleic acid introduction means as "transfection", "transformation" and "transduction".

The term "isolated" refers to material, such as a nucleic acid or a protein, which is substantially free from components that normally accompany or interact with it in its naturally-occurring environment. The isolated material optionally comprises material not found with the material in its natural environment or if the material is in its natural environment, the material has been synthetically (non-naturally) altered by human intervention to a composition and/or placed at a location in the cell (e.g., genome or subcellular organelle) not native to the isolated material. The alteration to yield the synthetic material can be performed on the material within or removed from its natural state. For example, a naturally-occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling, et al., PCT/US93/03868. Likewise, a naturally-occurring nucleic acid (e.g., a promoter) becomes isolated if it is introduced by non-naturally-occurring means to a locus of the genome not native to that nucleic acid.

As used herein, "nucleic acid" includes reference to a deoxyribonucleotide or ribonucleotide polymer or chimeras thereof, in either single- or double-stranded form, and unless otherwise limited, encompasses known analogues having the essential nature of natural nucleotides in that they hybridize to single-stranded nucleic acids in a manner similar to that of naturally-occurring nucleotides (e.g., peptide nucleic acids).

By "nucleic acid library" is meant a collection of isolated DNA or RNA molecules which comprise and substantially represent the entire transcribed fraction of a genome of a specified organism or of a tissue or cell type from that organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual*, 2nd ed., Vol. 1-3 (1989) and *Current Protocols in Molecular Biology*, Ausubel et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, cells isolated from seeds, suspension cultures, embryos, meristematic regions, callus tissue, leaves, roots, shoots, gametophytes, sporophytes, pollen and microspores. The class of plants which can be used in the methods of the invention include both monocotyledonous and dicotyledonous plants. A particularly preferred plant is Zea mays.

As used herein, "polynucleotide" includes reference to a deoxyribopolynucleotide, ribopolynucleotide or chimeras or analogs thereof that have the essential nature of a natural deoxy- or ribo-nucleotide in that they hybridize, under stringent hybridization conditions, to substantially the same nucleotide sequence as do naturally-occurring nucleotides and/or allow translation into the same amino acid(s) as do the naturally-occurring nucleotide(s). A polynucleotide can be full-length or a subsequence of a native or heterologous structural or regulatory gene. Unless otherwise indicated, the term includes reference to the specified sequence as well as to the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to naturally-occurring amino acid polymers, as well as to amino acid polymers in which one or more amino acid residue is an artificial chemical analogue of a corresponding naturally-occurring amino acid. The essential nature of such analogues of naturally-occurring amino acids is that, when incorporated into a protein, that protein is specifically reactive to antibodies elicited to the same protein but consisting entirely of naturally-occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. Further, this invention contemplates the use of both the methionine-containing and the methionine-less amino terminal variants of proteins of the invention.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is a plant cell. Exemplary plant promoters include, but are not limited to, those that are obtained from plants, plant viruses and bacteria which comprise genes expressed in plant cells such Agrobacterium or Rhizobium. Examples of promoters under developmental control include promoters that preferentially initiate transcription in certain tissues, such as leaves, roots or seeds. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions or the presence of light. Tissue specific, tissue preferred, cell type specific and inducible promoters constitute the class of "non-constitutive" promoters. A "constitutive" promoter is a promoter which is active under most conditions.

As used herein "recombinant" includes reference to a cell or vector that has been modified by the introduction of a heterologous nucleic acid or to a cell derived from a cell so modified. Thus, for example, recombinant cells express genes that are not found in identical form within the native (non-recombinant) form of the cell or express native genes that are otherwise abnormally expressed, under-expressed or not expressed at all, as a result of human intervention. The term "recombinant" as used herein does not encompass the alteration of the cell or vector by naturally-occurring events (e.g., spontaneous mutation, natural transformation/transduction/transposition) such as those occurring without human intervention.

Although the present invention has been described in some detail by way of illustration and example for purposes of clarity of understanding, it will be obvious that certain changes and modifications may be practiced within the scope of the appended claims.

EXAMPLES

Example 1: Silk Counting Protocol

The method determines the effect of transgene of yield or yield potential early in the transgene evaluation process. It allows prediction of the enhancement of a transgene on harvestable yield in T1 generation, without going through the time consuming yield trial.

T1 Plants to be Evaluated

The constructs evaluated in T1 silk number assay are selected based on their performance in yield related traits at T0 generation. T1 seeds are generated by crossing T0 hemizygous plants by fast growing, short stature inbred.

Growing Conditions

Each T1 plant is grown in a classic 200 size pot (volume equivalent to 1.7 L) labeled with a bar coded label with information about the plant's genetic identity, planting date and greenhouse location. The planting density is 8.5" between plants (~72K plants/acre). T1 seeds are sown in 50% Turface and 50% SB300 soil mixture at a uniform depth of 2" from the surface. Transgenic plants and their non-transgenic segregants were identified through strip test, assaying the presence of a marker gene linked with gene of interest.

Experimental Design

A nested block design with stationary blocks was used to minimize spatial variation. Experiment is blocked by events and constructs. Multiple events were evaluated for each constructs. For each event 15 transgene positive plants and 11 to 12 transgene negative plants were used. Positives and negatives are completely randomized within each event block. The transgene negative plants from events of the same construct were pooled together and used as construct null.

Silk Cutting

Silk was harvested at 8 days after silking using a cutting device. The silk pieces were deposited in a 20 ml scintillation vial temporarily attached to the cutting device. Residual silk pieces are rinsed into the vial with ~10 ml 90% ethanol applied by hand from a squirt bottle. The alcohol rinse here not only ensures that all silks are deposited in the vial but also reduces build up of sugary residues on the blades. Vials are labeled by writing EU-ID on the vial or alternatively the vials can be pre-labeled with bar codes containing info needed for sampled recognition.

Silk Number Determination Silk number determination was carried out using ImagePro silk counting software. For each sample, the contents of the vial are poured into a glass Petri dish 7.5 cm diameter and with walls 14 mm high, placed on dark navy blue or black background under a digital CDD (Q-imaging) camera connected to a PC equipped with ImagePro. The layer of liquid should be about 0.5 cm deep. Any contaminations such as anthers or husk tips are removed. The sample is allowed to settle for 5 seconds before the imaging.

Other Parameters Collected During T1 Yield Assay

In addition to silk numbers, scientists collected other data for parameters such as specific growth rate and maximum total area. The specific growth rate is the plant growth rate during exponential growth period. Maximum total area are the maximum biomass based on the three dimensional imaging of Lemna Tec. Shedding and silking data are also collected.

Example 2: Assessing the Correlation Between Silk Number and Spikelet Number Using a Dwarf Non-Transgenic Maize Line As shown in FIG. 1, silk number represents potential kernel number of a plant and can be used to represent the realizable yield potential under defined environmental condition. Kernel set is the result of a reduction from this potential as pollination and kernel abortion under the same environmental condition impact the success of an individual plant to produce kernels.

Assessing the Repeatability and Reproducibility of the Silk Counting Software

ImagePro Plus software was used to count the silk number. To assess the repeatability and reproducibility of the silk counting equipment, the silk number was counted multiple times and the instrumental variability was calculated. The variability of silk number was found to be less than 0.5% using the same sample multiple times by a single operator or multiple operators. The silk number determined by silk counting software correlated extremely well ($R^2$=0.99) with silk number determined by hand counting.

Silking Cutting Time

Figure 2:
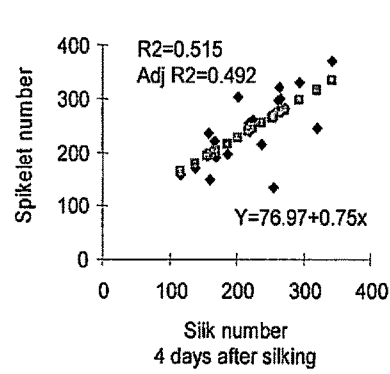
FIG. 2 shows graphs of the correlation between spikelet number and silk number collected at different intervals (days after silking).
Figure 2:
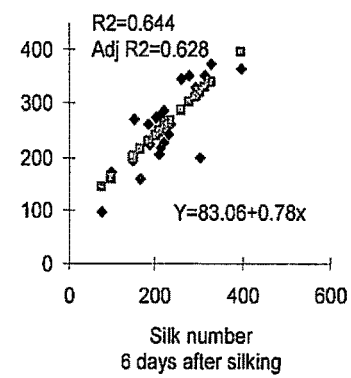
Figure 2:
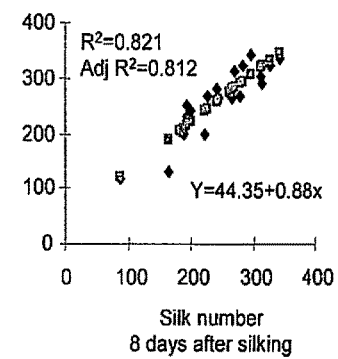

Several experiments were carried out to see whether the silk number is consistent enough among plants to be used effectively in an assay experiment. Results from these experiments showed a significant correlation between silk number and spikelet number, another good indicator of yield potential, further confirming the validity of silk number as an indicator of yield potential. Silk counting experiments were carried out for FAST corn maize plants under three different fertilizer application schemes and at 3 different dates (4, 6 and 8 days after silking). The experiment results showed that the correlation between silk number and spikelet number was best when fertilizer were applied once every two days or when silk counting was carried out at 8 days after silking (FIG. 2). As shown in Table 1, the variation of silk number among plants was lowest when silk counting was carried out 8 days after silking.

TABLE 1

Silk number and their CV at different silk cutting dates

| Silk cutting time (days after silking) | Silk number | Standard deviation | Coefficient of Variation |
|---|---|---|---|
| 4 | 217 | 60.07 | 27.68 |
| 6 | 229 | 73.97 | 32.3 |
| 8 | 246 | 60.93 | 24.77 |

Example 3: T1 Silk Number Assay on Transgenic Lines to Identify Constructs that would Enhance Yield/Yield Potential To assess the efficacy of the T1 yield assay, 15 potential yield enhancement constructs selected based on their T0 performance in yield related traits were evaluated. Three events were evaluated for each construct. For each event, 15 transgene positive plants and 11-12 transgene negative plants were used. A nested block design with stationary blocks was used to minimize spatial variation. Experiments were blocked by events and constructs. Positives and negatives were completely randomized within each event block. Transgene negative plants from all events of a single construct then were pooled together and used as construct null.

As summarized in Table 2, among the fifteen GOI (gene of interest) constructs assayed, six constructs were able to significantly increase the yield potential as defined by silk number. Two of the constructs significantly decreased the yield potential. The assay also showed that the increased yield potential was not always associated with plant growth or biomass. Two of the constructs assayed (PHP27561 and PHP30542) have very close correlation with either specific growth rate or maximum area or both.

TABLE 2

Percent change in silk number, specific growth rate and maximum area

| | Silk number | | Specific growth rate | | Maximum area | |
|---|---|---|---|---|---|---|
| GOI construct ID | % change | P value | % change | P value | % change | P value |
| PHP22743 | 11.2 | NS | 7.2 | 0.0191 | 2.59 | NS |
| PHP24878 | −11.3 | −0.0575 | −0.1 | NS | 3.6 | NS |
| PHP25433 | −6.73 | −0.0447 | 3.6 | 0.0269 | −3.89 | −0.0158 |
| PHP25445 | 10.83 | 0.0079 | −1.5 | NS | 0.5 | NS |
| PHP25872 | 4.1 | NS | 0.7 | NS | 5.3 | NS |
| PHP27215 | −2.97 | NS | 1.4 | NS | 2.14 | NS |
| PHP27540 | 9.07 | 0.0646 | 1 | NS | −0.44 | NS |
| PHP27561 | 20.16 | 0.0020 | 10.80 | 0.0001 | 5.44 | 0.0447 |
| PHP27893 | 0 | NS | 0.55 | NS | 1.02 | NS |
| PHP27958 | 12.5 | 0.0339 | −1.2 | NS | −2.4 | NS |
| PHP28098 | 4.29 | NS | −0.6 | NS | 3.26 | 0.0708 |
| PHP28100 | 23.29 | 0.0000 | 0.6 | NS | 4.63 | 0.0257 |
| PHP28126 | 2.42 | NS | 1.6 | NS | −0.57 | NS |
| PHP30542 | 15.55 | 0.0427 | 4.9 | 0.0977 | 11.5 | 0.0417 |
| PHP32787 | −3.6 | NS | 0.4 | NS | −2.53 | −0.0407 |

Table 3 shows the data for the three individual PHP27561 events assayed. Among the three events assayed, two of the events have significantly increased silk numbers. Importantly, the increased silk number is highly correlated with the expression of GOI in the construct.

TABLE 3

T1 silk number assay summary for PHP27561

| GOI construct ID | Relative event | GOI expression | Silk number % change | P value | Specific growth rate % change | P value | Maximum area % change | P value |
|---|---|---|---|---|---|---|---|---|
| PHP27561 | all | | 20.16 | 0.0020 | 20.16 | 0.0001 | 5.54 | 0.0447 |
| | 1 | −0.13 | 4.03 | NS | 3.79 | NS | 4.84 | NS |
| | 2 | 5.00 | 24.51 | 0.0115 | 6.85 | 0.0085 | 3.19 | NS |
| | 3 | 6.28 | 25.75 | 0.0347 | 18.58 | 0.0009 | 30.02 | 0.0093 |

Example 4: The Comparison of T1 Yield Assay Results with Yield Trial Results in the Field To assess the efficacy of T1 yield assay, 8 constructs were retransformed into elite maize. Single copy transgenic events with transgene expression were selected for fixing transgene and for seed increase. Top cross seeds were generated for yield trial. All events and controls were randomized in an Alpha array across the replicates. 10% of isogenic controls (construct null) are included in the trial. The yield of these transgenic events was analyzed against their construct nulls.

As summarized in Table 4, among the 8 constructs evaluated in both T1 yield assay and yield trials, six constructs showed very good correlation between T1 assay results and yield trial results. All four constructs that did not perform well in GH did not perform well in yield trial. Half of the constructs that performed positively or somewhat positively in T1 yield assay have good performances in yield trial. The T1 yield assay seems to be a very effective lead discovery and validation tool.

TABLE 4

Comparison of T1 yield assay and yield trial results in the field
(Significant when greater or less than control at p < 0.05)

| Constructs | T1 yield assay | Yield trial in the field |
|---|---|---|
| PHP25433 | Significantly less silks and shorter ears at silk suiting | Significantly less yield compared with control Null |
| PHP25872 | No effect on silk number and ear length | No effect on yield |
| PHP27495 | No effect on silk number and ear length | No effect on yield |
| PHP27540 | No effect on silk number and ear length | No effect on yield |
| PHP27561 | Significantly more silks and longer silk cutting | No effect on yield |
| PHP28100 | Significantly more silks and longer ears at silk cutting | Significantly more yield compared with control Null |
| PHP30532 | Significantly more silks and longer ears at silk cutting | Significantly more yield compared with control Null |
| PHP30542 | Significantly more silks and longer ears at silk cutting | No effect on yield |

The above examples are provided to illustrate the invention but not to limit its scope. Other variants of the invention will be readily apparent to one of ordinary skill in the art and are encompassed by the appended claims. All publications, patents, patent applications and computer programs cited herein are hereby incorporated by reference.

What is claimed is:

1. A method for screening for potential enhanced yield in maize, comprising:
    a. growing a maize plant under plant growing conditions until silks develop, wherein the maize plant comprises a heterologous polynucleotide encoding a polypeptide;
    b. counting the number of silks present in the maize ear;
    c. comparing the number of silks in the maize plant with the heterologous polynucleotide with a control maize plant that does not comprise the heterologous polynucleotide; and
    d. identifying the maize plant with an increased silk number when compared to the control maize plant, wherein said identified maize plant has potentially enhanced yield.

2. The method of claim 1, wherein the maize plant is an inbred or a hybrid.

3. The method of claim 1, wherein a plurality of maize plants are screened.

4. The method of claim 3, wherein the maize plants are grown in a greenhouse.

5. The method of claim 1, wherein the maize plant is a dwarf maize plant.

* * * * *